United States Patent
Wang et al.

(10) Patent No.: US 8,758,243 B2
(45) Date of Patent: Jun. 24, 2014

(54) SYSTEM AND METHOD FOR DIAGNOSING SLEEP APNEA BASED ON RESULTS OF MULTIPLE APPROACHES TO SLEEP APNEA IDENTIFICATION

(75) Inventors: Hui Wang, San Ramon, CA (US); Scott Amundson, Oakland, CA (US); Robin Boyce, Pleasanton, CA (US); James Ochs, Seattle, WA (US); Li Li, Milpitas, CA (US); Steven Vargas, Sun Valley, CA (US); Tonia Madere, Stockton, CA (US)

(73) Assignee: Covidien LP, Mansfield, MA (US)

( * ) Notice: Subject to any disclaimer, the term of this patent is extended or adjusted under 35 U.S.C. 154(b) by 260 days.

(21) Appl. No.: 13/019,882

(22) Filed: Feb. 2, 2011

(65) Prior Publication Data
US 2011/0190599 A1 Aug. 4, 2011

Related U.S. Application Data

(60) Provisional application No. 61/300,557, filed on Feb. 2, 2010.

(51) Int. Cl.
| | |
|---|---|
| *A61B 5/00* | (2006.01) |
| *G06K 9/62* | (2006.01) |
| *A61B 5/1455* | (2006.01) |
| *A61B 5/04* | (2006.01) |
| *A61B 5/0402* | (2006.01) |
| *G06F 19/00* | (2011.01) |
| *G06K 9/00* | (2006.01) |

(52) U.S. Cl.
CPC ............ *G06F 19/34* (2013.01); *G06F 19/3443* (2013.01); *G06F 19/345* (2013.01); *G06F 19/3487* (2013.01); *G06K 9/00496* (2013.01); *G06K 9/6292* (2013.01); *G06K 9/6293* (2013.01); *G06K 9/6256* (2013.01); *A61B 5/4818* (2013.01); *A61B 5/14551* (2013.01); *A61B 5/04* (2013.01); *A61B 5/04004* (2013.01); *A61B 5/0402* (2013.01); *A61B 2505/01* (2013.01); *A61B 2505/03* (2013.01); *Y10S 128/92* (2013.01); *Y10S 128/923* (2013.01); *Y10S 128/924* (2013.01); *Y10S 128/925* (2013.01); *Y10S 706/924* (2013.01)
USPC .......... 600/301; 600/323; 600/529; 128/920; 128/923; 128/924; 128/925; 702/19; 706/15; 706/20; 706/21; 706/924; 706/52

(58) Field of Classification Search
CPC .............. G06F 19/3443–19/345; G06F 19/34; G06F 19/3487; A61B 5/1455; A61B 5/14551; A61B 5/4818; G06K 9/6256; G06K 9/00496–9/0057; G06K 9/6267–9/6293
USPC .............. 706/20, 21, 924; 600/300–301, 323, 600/324, 364, 484
See application file for complete search history.

(56) References Cited

U.S. PATENT DOCUMENTS

| | | | |
|---|---|---|---|
| 3,926,177 A | | 12/1975 | Hardway, Jr. et al. |
| 4,696,307 A | | 9/1987 | Montgieux |
| 5,143,078 A | | 9/1992 | Mather et al. |
| 5,819,007 A | * | 10/1998 | Elghazzawi ................... 706/46 |
| 5,953,713 A | | 9/1999 | Behbehani et al. |
| 6,070,098 A | | 5/2000 | Moore-Ede et al. |
| 6,290,654 B1 | * | 9/2001 | Karakasoglu ................. 600/529 |
| 6,594,512 B2 | * | 7/2003 | Huang .......................... 600/324 |
| 6,918,878 B2 | | 7/2005 | Brodnick |
| 7,096,125 B2 | * | 8/2006 | Padmanabhan et al. ........ 702/24 |
| 7,190,995 B2 | | 3/2007 | Chervin et al. |
| 7,315,753 B2 | * | 1/2008 | Baker et al. ................... 600/323 |
| 7,507,207 B2 | | 3/2009 | Sakai et al. |
| 2001/0018557 A1 | | 8/2001 | Lynn et al. |
| 2004/0254481 A1 | | 12/2004 | Brodnick |
| 2005/0286772 A1 | * | 12/2005 | Albertelli ...................... 382/224 |
| 2007/0118054 A1 | | 5/2007 | Pinhas et al. |
| 2007/0282212 A1 | | 12/2007 | Sierra et al. |
| 2008/0119756 A1 | | 5/2008 | Wada |
| 2010/0063366 A1 | * | 3/2010 | Ochs et al. ................... 600/301 |
| 2010/0113909 A1 | | 5/2010 | Batchelder |
| 2011/0251985 A1 | * | 10/2011 | Waxman et al. ................ 706/20 |

FOREIGN PATENT DOCUMENTS

| | | |
|---|---|---|
| EP | 178197 | 5/1989 |
| EP | 1512430 | 3/2005 |
| EP | 1740095 | 1/2007 |
| EP | 1821076 | 8/2007 |
| WO | 2005009631 | 10/2005 |
| WO | 2008122806 | 10/2008 |

OTHER PUBLICATIONS

Marcos, J.V. et al "Applying Neural Network Classifiers in the Diagnosis of the Obstructive Sleep Apnea Syndrome from Nocturnal Pulse Oximetric Recordings", Proceedings of the 29th Annual International Conference of the IEEE EMBS, Cité Internationale, Lyon, France, Aug. 23-26, 2007; p. 5174-5177.*

Figliola, A. et al; "Analysis of Physiological Time Series Using Wavelet Transforms"; IEEE in Medicine and Biology; May-Jun. 1997; p. 74-79.*

Fontela-Romero, O. et al; "A new method for sleep apnea classification using wavelets and feed forward neural networks"; Artificial Intelligence in Medicine (2005) 34, p. 65-76.*

Lee, Y. K. et al; "Automated detection of obstructive apnea and hypopnea events from oxygen saturation signal"; Proceedings of the 26th Annual International Conference of the IEEE EMBS San Francisco, CA, USA • Sep. 1-5, 2004: p. 321-324.*

Marcos, J. V. et al; "Assessment of four statistical pattern recognition techniques to assist in obstructive sleep apnoea diagnosis from nocturnal oximetry"; Medical Engineering & Physics 31 (2009) p. 971-978.*

Sohl, A. Al. et al; "Validity of Neural Network in sleep Apnea"; Sleep; vol. 22; No. 1, 1999; p. 105-111.*

Weinreich, G. et al; "Pattern recognition of obstructive sleep apnoea and Cheyne-Stokes respiration"; Physiol. Meas. 29 (2008) p. 869-878.*

Chow, H-S. et al; "Detection of Ventricular Ectopic Beats Using Neural Networks"; IEEE, 1992; p. 659-662.*

Borgel, J. et al. "Central Sleep Apnea Induces Ventricular Bigeminus. Conclusions from a single polygraphy"; Circulation. 2008;118:1398-1401.*

International Search Report with Written Opinion issued in International Application No. PCT/US2011/023476 dated May 6, 2011 (15 pages).

* cited by examiner

*Primary Examiner* — Gary Jackson
*Assistant Examiner* — Marie Archer
(74) *Attorney, Agent, or Firm* — Fletcher Yoder PC

(57) ABSTRACT

Various embodiments may provide methods and systems capable of evaluating physiological parameter data. The methods and systems may include a receiver capable of collecting a signal representative of a physiological status of a patient, a plurality of data analysis components, wherein each of the plurality of data analysis components is capable of generating a metric based on the signal, and an arbitrator communicatively coupled to each of the plurality of data analysis components and capable of generating a single metric from the metrics generated by the plurality of data analysis components.

17 Claims, 4 Drawing Sheets

SYSTEM AND METHOD FOR DIAGNOSING SLEEP APNEA BASED ON RESULTS OF MULTIPLE APPROACHES TO SLEEP APNEA IDENTIFICATION

RELATED APPLICATIONS

This application claims the benefit of U.S. Provisional Application No. 61/300,557 filed Feb. 2, 2010, which application is hereby incorporated herein by reference.

BACKGROUND

1. Technical Field

Embodiments in accordance with the present disclosure relate to a system and method for evaluating physiological parameter data. Specifically, an embodiment may include a system capable of arbitrating results from multiple approaches to identification of sleep apnea based on measured physiological parameters.

2. Description of the Related Art

This section is intended to introduce the reader to various aspects of art that may be related to various aspects of the present disclosure, which are described and/or claimed below. This discussion is believed to be helpful in providing the reader with information to facilitate a better understanding of the disclosure. Accordingly, it should be understood that these statements are to be read in this light, and not as admissions of prior art.

Sleep apnea is a medical condition that may be defined as a temporary suspension of breathing that occurs repeatedly during sleep. Sleep apnea may take several forms. For example, sleep apnea may be classified as obstructive sleep apnea, central sleep apnea, or complex sleep apnea. Each of these forms of sleep apnea may be distinguished based on the causes associated with the particular type of sleep apnea. For example, obstructive sleep apnea, which is believed to be one of the most common disorders in the United States and an important cause of heart attack and stroke, typically occurs as the result of an obstruction, such as the relaxation of muscles in the back of the throat. Central sleep apnea, on the other hand, is not caused by an obstruction but by a neurological failure. For example, central sleep apnea may be described as the result of a central nervous system disorder wherein the body essentially fails to provide a neurological signal indicating that the body should breathe. Complex sleep apnea may be defined as a combination of obstructive sleep apnea and central sleep apnea.

Various approaches exist that may be utilized to diagnose sleep apnea. For example, various existing tests and algorithms may be used to identify and/or quantify indications of sleep apnea based on physiological measurements. Depending on circumstances, the results of some approaches may be better than others. For example, some approaches may be directed to analyzing a substantial amount of physiological data, while other approaches may be directed to providing an indication of sleep apnea based on a relatively small amount of recent data observed within a moving window of time. Further, some approaches may be based on the use of more or fewer inputs, different assumptions, the use of differing equipment, and so forth. Accordingly, depending on the approach utilized, different results may be obtained with regard to indications of sleep apnea based on the same patient's physiological data.

BRIEF DESCRIPTION OF THE DRAWINGS

Advantages of the techniques may become apparent upon reading the following detailed description and upon reference to the drawings in which.

DETAILED DESCRIPTION

Figure 1:
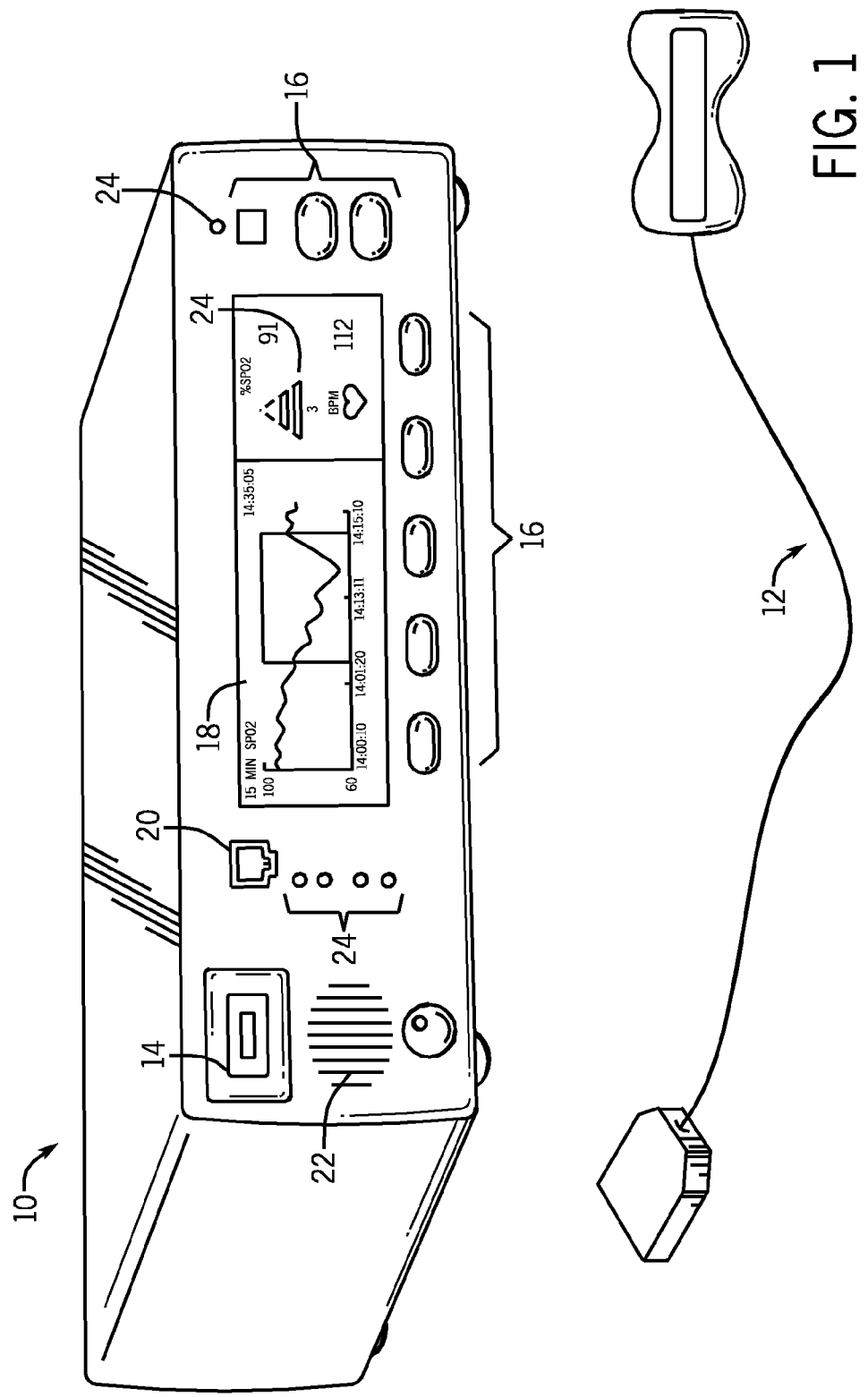
FIG. 1 is a perspective view of a patient monitoring system in accordance with various embodiments.

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another, Moreover, it should be appreciated that such a development effort might be complex and time consuming, but would nevertheless be a routine undertaking of design, fabrication, and manufacture for one of ordinary skill having the benefit of this disclosure.

Medical devices, such as pulse oximetry monitors and sensors, may be used to monitor patients, and, thus, obtain signals that are representative of physiological parameters of the patients. The signals, which may be referred to as physiological signals or measurements may be utilized to diagnose certain medical conditions. For example, certain patterns observed in a trend of a patient's pulse oximetry data may indicate that the patient is suffering from sleep apnea. However, these signals, which are typically sequences of numerical values corresponding to changing physiological parameter measurements over time, may have too much information or noise to be effectively used in the diagnosis or treatment of certain medical conditions. Accordingly, the signals may be processed to generate a secondary indicator of certain medical conditions, such as sleep apnea. Specifically, for example, a medical device may be capable of automatically analyzing a series of physiological measurements with an algorithm to derive an indication (e.g., an index value) or a series of indications (e.g., a trend of a continuously changing index) that may provide a more useful representation of the status of a medical condition or a diagnosis.

Various tests and algorithms exist that may be used to diagnose sleep apnea. For example, a patient monitor may utilize a specific data analysis algorithm to identify one or more patterns in a trend of physiological data, such as blood oxygen saturation data, that may be indicative of sleep apnea. Indeed, clusters of desaturation patterns in a trend of blood oxygen saturation data may be utilized to provide an indication of sleep apnea, as generally described in U.S. Pat. No. 5,891,023 and U.S. Pat. No. 6,223,064, each of which is herein incorporated by reference in its entirety. As another example, a patient monitor may be configured to identify sleep apnea based on correlations between a patient's measured physiological parameters and sleep lab data. For example, sleep apnea may be diagnosed utilizing an overnight sleep test referred to as a polysomnogram, which is generally performed in a sleep lab and involves the continuous and simultaneous measurement and recording of an encephalogram, an electromyogram, an extraoculogram, a chest wall plethysmogram, an electrocardiogram, measurements of nasal and oral airflow, and pulse oximetry. All or some of these and other channels may be measured throughout the night, and complex recordings of such measurements may then be analyzed by a highly trained clinician or a device configured to analyze the data using an automated algorithm to determine the presence or absence of sleep apnea, as described in U.S. patent application Ser. No. 12/208,087, which is incorporated herein by reference in its entirety.

Numerous examples of procedures for analyzing physiological data to diagnose sleep apnea are available, and each procedure may provide a different result based on physiological measurements obtained from the same patient during the same period of time. Indeed, depending on conditions and/or limitations relating to the available data, certain approaches to sleep apnea diagnosis may be more accurate and/or faster than others. The accuracy and/or speed of a particular approach may depend on aspects relating to the measurement of the physiological parameters, the parameters themselves, and/or the nature of the desired measurement (e.g., a real-time diagnosis of sleep apnea or a diagnosis based on data from a full period of sleep). For example, a particular approach may be more accurate when a certain amount of data is available, when certain assumptions are more accurate, and/or when a particular type of measurement device is used to obtain the physiological parameters being analyzed. With regard to the parameters being utilized, a particular approach that uses numerous parameters (e.g., values associated with an encephalogram, an electromyogram, extraoculogram, a chest wall plethysmogram, an electrocardiogram, measurements of nasal and oral airflow, and pulse oximetry) may have a more accurate result when substantial data is available, but the result may be more difficult and time consuming to acquire than using a method that simply uses parameters obtained via pulse oximetry.

Present embodiments are directed to a system and method for receiving and/or determining a plurality of sleep apnea indications based on physiological parameter values using various different approaches, and arbitrating the plurality of indications to provide a simplified indication (e.g., a single index value) related to sleep apnea. In accordance with present embodiments, arbitrating may include selecting one of a plurality of indicators and/or combining a plurality of indicators into a single indicator. For example, present embodiments may receive an index value representative of a level of sleep apnea from each of various different features and/or algorithms that utilize different approaches to the identification of sleep apnea, and then select a one of the plurality of index values for presentation as a reported value or resulting output. In other embodiments, indicators (e.g., index values for sleep apnea) from all or a portion of the various approaches to identification of sleep apnea may be combined to provide a single reported value. For example, the results from each of the various approaches may be weighted based on particular conditions surrounding their acquisition or the manner of observation, and the weighted values may then be combined in an algorithm to provide a single reported value. It should be noted that the reported value may be described as a system output. For example, the reported value may be displayed for review by a user on a display (e.g., a computer screen), output for use in a treatment feature (e.g., an air supply feature that is activated when the reported value is above or below a designated threshold value), and so forth.

FIG. 1 is a perspective view of a medical device 10 in accordance with various embodiments. The medical device 10 may have a sensor 12 for the collection of a signal representing a physiological parameter. For example, in one embodiment, the sensor 12 may be an optical sensor used with a pulse oximeter for the measurement of oxygen saturation ($SpO_2$) in the bloodstream. The device 10 may receive and condition the $SpO_2$ signal from the sensor 12 via an interface 14 prior to being utilized by a microprocessor in the device 10 or a networked component. The medical device 10 may include random access memory (RAM) and/or read-only memory (ROM). For example, the RAM may be used to store the signals from the sensor 12 and the results of calculations that the device 10 performs. The ROM may contain code to direct the device's microprocessor in collecting and processing the signal. The microprocessor may be connected to an input device 16 (e.g., control features on the face of the device 10 or a keyboard) which may be used for local entry of control and calculation parameters for the medical device 10. A display unit 18 may be included within or connected to the device 10 to display the results the microprocessor has generated from the signal.

The device 10 may also include a network interface 20 for the transfer of data between the device 10 and devices connected to a local area network. The transferred data may include various different parameter calculations that may be arbitrated by an arbitration feature of the medical device 10. Further, the transferred data may, for example, include signal data, indices including a saturation pattern detection index (e.g., a value selected or obtained from a plurality of index calculations), alarm signals, or any combination thereof. The transferred data may also consist of control signals to instruct the medical device 10 or the networked devices to provide signal data, or other information.

In an embodiment, the medical device 10 and/or various networked devices may be used to determine a plurality of parameter metrics (e.g., saturation pattern detection indices) with the data collected from the sensor 12 and/or various other sensors, and to combine the plurality of metrics into a single metric and/or select a one of the metrics as an output using an arbitration feature. For example, the device may be capable of quantifying multiple metrics for sleep apnea based on physiological parameter measurements, and arbitrating (e.g., selecting or combining) the results to provide a single indication of sleep apnea. The single metric may be referred to as a resulting index. The resulting index may then be output to the display unit 18, utilized as a treatment control, utilized to initiate an alarm (e.g., an audible alarm via a speaker 22 or a visual alarm via a visual indicator 24), sent to a network device on the local area network via the network interface 20, or the like.

Figure 2:
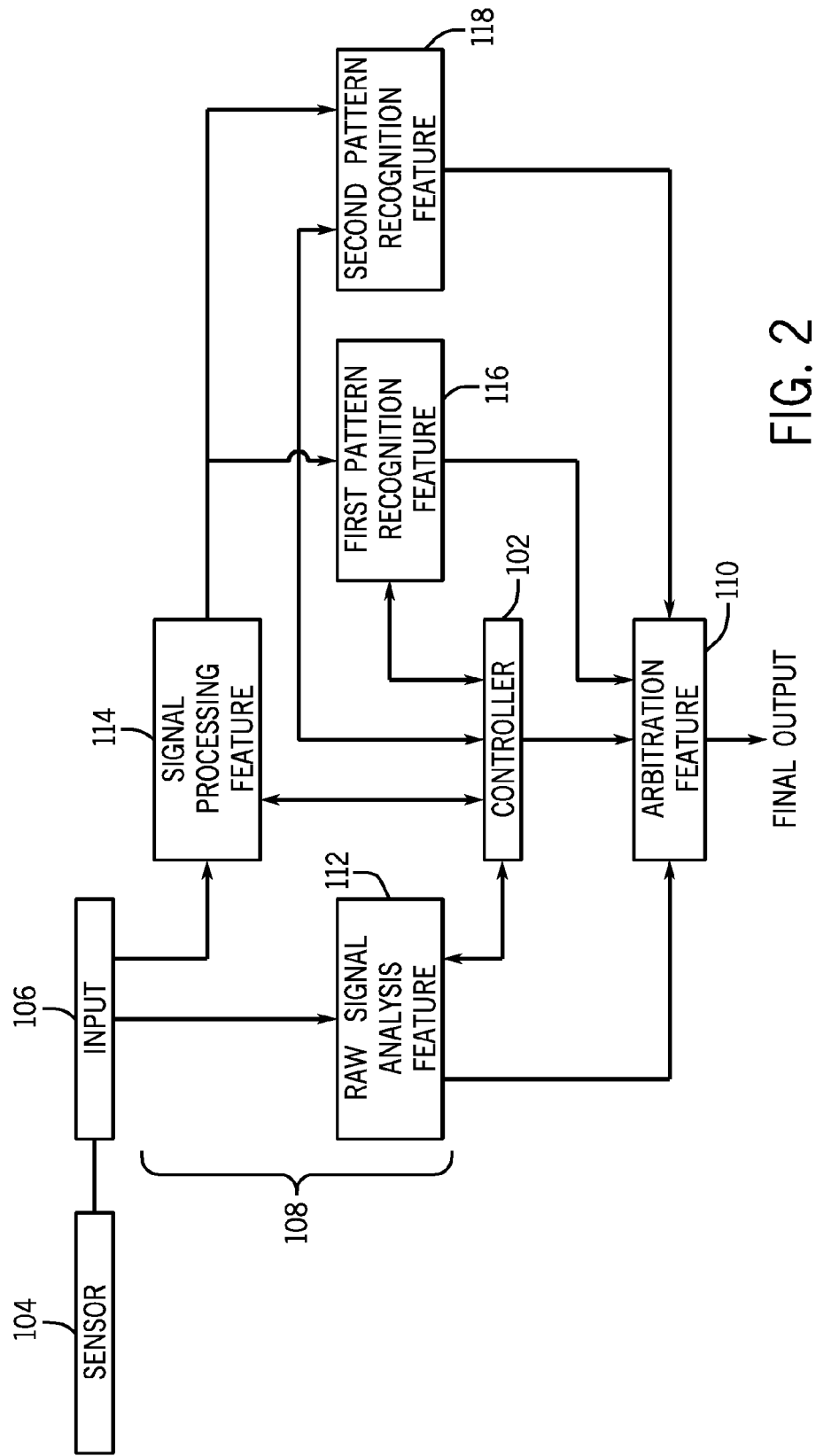
FIG. 2 is a block diagram of a method for applying and arbitrating between multiple procedures for diagnosing sleep apnea in accordance with various embodiments.

Present embodiments may include code stored on a tangible, computer-readable medium (e.g., a memory) and/or hardware capable of detecting the presence of a saturation pattern in a series of physiologic data. For example, FIG. 2 is a block diagram of a medical system including various physiological data analysis features in accordance with present embodiments. The system is generally indicated by the reference number 100. The system 100 may comprise a memory device and/or a computer that includes a microprocessor and a memory. For example, the system 100 may include an $SpO_2$ monitor and/or a memory device.

In the illustrated embodiment, the system 100 includes various subsystems represented as functional blocks in FIG. 1, wherein the operations of the various subsystems may be coordinated by a processor or controller 102. Those of ordinary skill in the art will appreciate that the various functional blocks shown in FIG. 1 may comprise hardware elements (e.g., circuitry), software elements (e.g., computer code stored on a hard drive) or a combination of both hardware and software elements. For example, each functional block may represent software code and/or hardware components that are configured to perform all or portions of one or more algorithms in accordance with present embodiments. Specifically, in the embodiment illustrated in FIG. 1, the system 100 includes the controller 102, a physiological sensor 104, a physiological signal input 106, a plurality of signal analysis features 108, and an arbitration feature 110. Each of these components and the coordination of their functions will be discussed in further detail below. It should be noted that the embodiment illustrated in FIG. 1 merely represents one embodiment, and other embodiments in accordance with the present disclosure may include numerous different signal inputs, signal processing features, and so forth.

The physiological sensor 104 may represent one or more system components capable of measuring physiological parameters of a patient, and the physiological signal input 106 may represent one or more system components capable of receiving signals from the sensor 104. The sensor 104 may include any of various types of sensors and the signal input 106 may be adapted to receive signals from any of various types of sensors. For example, the sensor 104 may include a pulse oximetry sensor that includes an emitter and a detector for non-invasively measuring blood oxygen saturation levels. Specifically, the sensor 104 may include an emitter adapted to emit certain wavelengths of light into a patient's tissue where blood perfuses the tissue, and a detector adapted to photoelectrically detect the light after passing through the tissue. Signals representative of detected light levels may be transmitted from the sensor 104 to the signal input 106 (e.g., a port or receiver) wirelessly or via a cable for use in estimating an amount of blood constituent present in a patient's tissue. In other embodiments, different and multiple sensors (e.g., an airflow sensor and a pulse rate sensor) may be used and the corresponding signals may be used to estimate different physiological parameter values.

In the illustrated embodiment, the plurality of signal analysis features 108 include a raw signal analysis feature 112, a signal processing feature 114, and a pair of pattern recognition features 116 and 118. The raw signal analysis feature 112 receives signals directly from the input 106, while the pair of pattern recognition features 116 and 118 each receive signal data from the signal processing feature 114 after the data has been processed. The signal processing feature 114 may be capable of receiving the physiological signal from the input 106 and converting the signal into a value representative of a physiological parameter. For example, the signal processing feature 114 may include an oximetry algorithm adapted to filter out noise and obtain a value of blood oxygen saturation based on the signal originating from the sensor 104. Indeed, the signal processing feature 114 may convert sensor signals into a series of physiological parameter values over time (e.g., a data trend).

Each of the signal analysis features 108 may be capable of defining a metric that is indicative of a certain detected condition (e.g., a level of sleep apnea). The raw signal analysis feature 112 may be capable of receiving a signal directly from the input 106, processing the signal, analyzing a series of signal values based on pattern recognition, and outputting an indication (e.g., a metric or index) of the analysis result. The pair of pattern recognition features 116 and 118 may be capable of detecting patterns in the series of physiological parameter values. For example, the pattern recognition features 116 and 118 may be capable of detecting clusters of desaturation patterns in the blood oxygen saturation values that may be indicative of sleep apnea. Further, the pair of pattern recognition features 116 and 118 may be capable of outputting an indication (e.g., a metric or index) of the presence and/or level of sleep apnea detected in the series of values.

The arbitration feature 110 may include a software component, a hardware component, or some combination thereof that is configured to produce a final output or adjusted range of outputs based on the results obtained by the plurality of signal analysis features 108. For example, in one embodiment, the arbitration feature 110 may include an algorithm for selecting a single output from one of the plurality of outputs of the signal analysis features 108 as a final output. In another embodiment, the arbitration feature 110 may combine two or more of the outputs from the plurality of signal analysis features 108 into a single, final output or a range of final outputs. For example, outputs from several of the signal analysis features 108 may be combined in an equation that gives a certain weight to each of the outputs and then combines the outputs into a single metric. For example, a sample equation that may be utilized to combine the metrics from the signal analysis features 106 may be generally represented:

$$\text{Final Metric} = a*A + b*B + c*C, \quad \text{(equation 1)}$$

where a, b, and c are percentage weighting values that combine to 100%, and A, B, and C represent the outputs from the raw signal analysis feature 112, the first pattern recognition feature 116, and the second pattern recognition feature 118, respectively. The constants a, b, and c may be predetermined (hard coded) numbers selected based on analysis of data during the algorithm development phase. In other embodiments, the constants a, b, and c may represent a confidence value computed by each of the pattern recognition features. In other embodiments, the arbitration feature 110 may select two or more of the results provided by the signal analysis features 108 and provide a range of potential values as the single, resulting output. It should be noted that in other embodiments, different numbers of signal analysis features 108 may be utilized. An artificial neural network may be trained to combine the output of the various pattern recognition features. The inputs to the neural network may be values A, B, and C, the confidence metrics a, b, and c, or any other metric within the system that would assist the network in determining the "best" combination of pattern recognition features to present to the user. In the case of a pulse oximetry system, one of these neural network input metrics may be an $SpO_2$ or pulse rate confidence metric. Once the single output is determined, it may be submitted to an output feature 120 (e.g., a display, a patient therapy control feature, an airflow controller, or the like).

Figure 3:
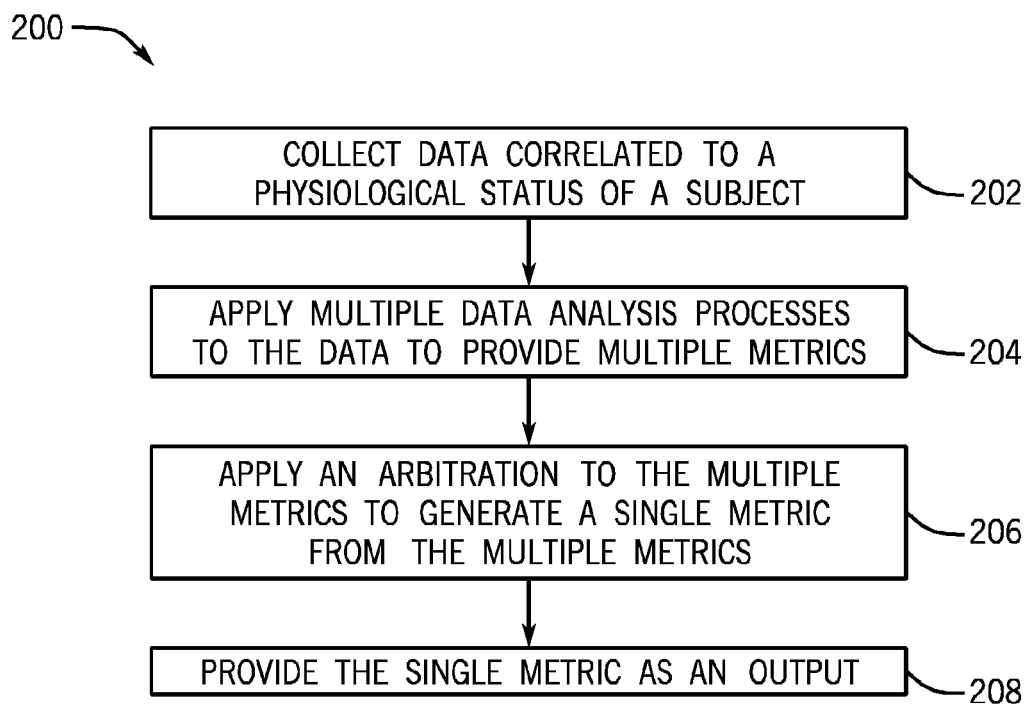
FIG. 3 illustrates a flow diagram of a method in accordance with various embodiments.

FIG. 3 illustrates a flow diagram of a method 200 in accordance with embodiments of the present disclosure, The method includes the application of multiple data processes to generate multiple metrics related to the detection of sleep apnea, and providing a single metric that is representative of sleep apnea based on the multiple metrics. The method 200 may be performed using a system that is specifically configured for performing the procedures of the method 200, such as the system 100. For example, the method may be performed with a system that includes hardware and/or software features for acquiring one or more signals representative of certain physiological parameters, analyzing the signals using different approaches, arbitrating between results obtained by the various approaches, and so forth.

In the illustrated embodiment, the method 200 begins with collecting data correlated to a physiological status of a subject, as represented by block 202. This act may include detecting physiological parameters with a sensor and collecting a sequence of signal values (e.g., trend data) over time in a memory (e.g., a hard drive). After such data is collected, the method 200 proceeds to apply multiple data analysis processes to the data to provide multiple metrics related to a patient's condition, as illustrated by block 204. For example, block 204 may represent analyzing pulse oximetry trend data and/or signal data with a patient monitor or various monitors in a monitoring system using various different tests and/or algorithms to determine whether patterns within the trend and/or signal data are indicative of sleep apnea. Further, block 204 may represent generating indicators (e.g., metrics or index values) that correspond to a presence and/or a level of sleep apnea suggested by the patterns. Once the multiple processes have been performed, arbitration may be applied to the multiple results to generate a single metric, as represented by block 206. For example, multiple metrics that are indicative of different levels of sleep apnea may be submitted to a hardware and/or software feature that is configured to analyze the metrics, and produce a final metric for an output based on the multiple metrics. Specifically, for example, metrics from each of the multiple processes may be passed through an arbitrator, such as the arbitration feature 110, which combines the metrics or selects a metric based on certain criteria (e.g., an assumed accuracy or desired speed). Once a single metric has been obtained, it may be presented as an output, as indicated in block 208.

Figure 4:
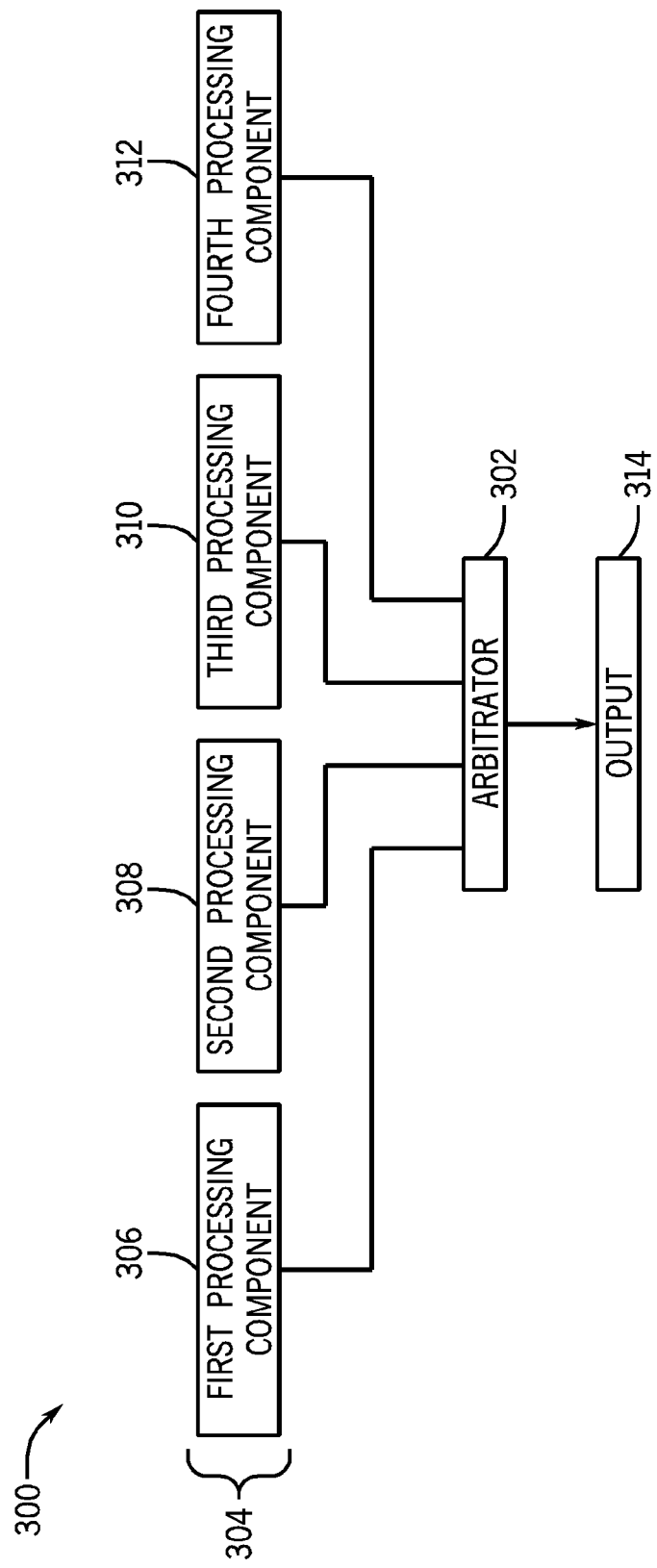
FIG. 4 is a block diagram that is representative of a system including an arbitrator and various pulse oximetry data processing components in accordance with present embodiments.

FIG. 4 is a block diagram that is representative of a system 300 including an arbitrator 302 and various pulse oximetry data processing components 304 in accordance with present embodiments. Specifically, in the illustrated embodiment, the processing components 304 include a first processing component 306, a second processing component 308, a third processing component 310, and a fourth processing component 312. In other embodiments, more or fewer processing components may be included. Each of the processing components 304 may be configured to analyze pulse oximetry data (e.g., a series of measured blood oxygen saturation levels) using different procedures or algorithms for identification of blood oxygen saturation patterns. Further, each of the processing components 304 may be configured to provide a metric representative of certain data patterns, such as patterns indicative of ventilatory instability or sleep apnea, In other words, for example, the processing components 304 may each be configured for saturation pattern detection and reporting of a value or index that is representative of a condition associated with the detected patterns. For example, in one embodiment, each of the processing components 304 may produce a saturation pattern detection index (SPDi) that is indicative of a level of sleep apnea based on observed pulse oximetry data.

As indicated above, different algorithms may be utilized by each of the processing components 304. Further, different algorithms may be more suited for making an accurate determination depending on certain variables. For example, the first processing component may provide the most accurate estimate when the input signals are relatively noise free. The second processing component may be the most accurate during periods of motion induced artifact. The third processing component may be most accurate when patterns are very mild, when patients are on supplemental oxygen for example. The arbitrator may use various input variables, such as noise metrics computed by an $SpO_2$ algorithm or user settings to determine which processing component or combination of processing components will give the most accurate readings.

The first processing component 306 may provide the most accurate estimate of a level of sleep apnea when more than 4 hours of data is available, the second processing component 308 may be more suited for identifying alarm conditions, the third processing component 310 may provide the most accurate estimate of a level of sleep apnea when multiple types of data (e.g., data reflective of pulse rate, breathing rate, and airflow into the lungs) are available, and the fourth processing component 312 may be more suited for spot measurements. In view of these distinctions, depending on the purpose for monitoring a patient and/or other circumstances, different processing components may be preferred based on a prediction of their accuracy in view of the circumstances. Accordingly, present embodiments may utilize the arbitrator 302 to combine and/or select between calculated metrics from the different processing components 304 based on the purpose of the monitoring and/or based on the nature of the algorithms performed by the processing components. Once selected and/or combined, the single metric may be submitted as an output 314 by the arbitrator 302 for use as a set point, indicator, displayed metric, or the like.

As a specific example, in one embodiment, the first processing component 306 may be capable of performing a sleep lab data analysis that is adapted for analyzing sleep data from a complete sleep cycle including various measured parameters in addition to blood oxygen saturation to provide a sleep apnea metric, and the second processing component 308 may be capable of providing a sleep apnea metric based solely on pulse oximetry data acquired within a limited time window (e.g., a 15 minute window). Thus, the reliability of the output from the first processing component 306 may improve as more data is acquired and when all of the proper sensors are active, while the reliability of the second processing component 308 may remain consistent over time based on a single sensor but with limited accuracy.

Variables, such as available sensor inputs and quantity of available data, may be monitored by the arbitrator 302 and the output from the first and second processing components 306 and 308 may be weighted based on these variables and/or the purpose of the monitoring. For example, if the purpose of monitoring is to obtain a sleep apnea diagnosis based on a full set of sensor data obtained during a complete sleep cycle, the output from the first processing component 306 may be much more heavily weighted than an output from the second processing component 308. If the purpose is to continuously monitor over time, the output from the first processing component 306 may be increasingly weighted as time passes and more data becomes available. In some instances, the output from the first processing component 306 may be blocked until a threshold amount (e.g., 1 hour) of data is available. The weighting associated with the outputs may be utilized to select an output for display and/or the weighting may be used to combine the outputs from various algorithms in a desired proportion, as indicated by Equation 1 discussed above. It should be noted that while only two analysis approaches are utilized in the example discussed above, weighting schemes and so forth could be applied to any number of different algorithms and/or processing components.

As discussed above and as will be appreciated by one of ordinary skill in the art, different algorithms for identifying patterns indicative of sleep apnea in physiological data may each perform better under different circumstances and/or depending upon the purpose of performing an analysis. For example, different algorithms may be more appropriate for providing a metric indicative of sleep apnea based on a single or multiple different physiological parameters, long or short periods of observation, and so forth. Similarly, different algorithms may be better equipped for different purposes, such as the purpose of alarming, analyzing data, and so forth. Accordingly, outputs of the processing components 304 may be weighted accordingly. Such weighting may be implemented as a factory setting and/or as a user setting. Indeed, in accordance with present embodiments, the weighting may be entered by a user and associated with a particular type of algorithm. The weighting may be based on the type of data available, the quantity of data available, the purpose for monitoring, and so forth. In other words, the weighting may be based on a predicted accuracy under existing circumstances. Further, as discussed above, the weighting may be utilized to select and/or combine various metrics to define a single metric for use in control (e.g., supply of air to a patient to stop the sleep apnea) and/or for presentation to a user as indicative of a patient's condition.

While the disclosure described above may be susceptible to various modifications and alternative forms, various embodiments have been shown by way of example in the drawings and have been described in detail herein. However, it should be understood that the disclosure is not intended to be limited to the embodiments for calculating saturation pattern detection index presented herein. Rather, the disclosure is to cover all modifications, equivalents, and alternatives falling within the spirit and scope of the disclosure as defined by the following appended claims.

What is claimed is:

1. A method of determining the physiological status of a patient, comprising:
    monitoring the patient with at least one sensor to produce physiological parameter data comprising a sequence indicative of blood oxygen saturation over a time period;
    analyzing the physiological parameter data with a first pattern recognition feature to identify indications of sleep apnea;
    calculating a first sleep apnea metric with the first pattern recognition feature based on indications of sleep apnea identified by the first pattern recognition feature in the physiological parameter data;
    analyzing the physiological parameter data with a second pattern recognition feature to identify indications of sleep apnea;
    calculating a second sleep apnea metric with the second pattern recognition feature based on indications of sleep apnea identified by the second pattern recognition feature in the physiological parameter data;
    applying an arbitration with an arbitrator to the first and second sleep apnea metrics to determine a single sleep apnea metric, wherein applying the arbitration further comprises assigning a weighted value to each of the sleep apnea metrics based on a type of algorithm performed by the pattern recognition feature associated with each metric; and
    communicating the single sleep apnea metric to an output feature to display as an indication of the patient's status and/or to control a therapeutic device.

2. The method of claim 1, comprising monitoring the patient with a plurality of sensors to produce physiological parameter data comprising an encephalogram, an electromyogram, an extraoculogram, a chest wall plethysmogram, and/or an electrocardiogram.

3. The method of claim 1, comprising monitoring the patient with a plurality of sensors to produce physiological parameter data comprising measurements of nasal and/or oral airflow.

4. The method of claim 1, comprising determining that an indication of sleep apnea is present with the first pattern recognition feature and/or the second pattern recognition feature when a number of desaturation patterns within the time period is identified in the physiological parameter data.

5. The method of claim 1, wherein applying the arbitration comprises selecting a one of the sleep apnea metrics as the single sleep apnea metric.

6. The method of claim 1, wherein applying the arbitration comprises combining the first and second sleep apnea metrics to determine the single sleep apnea metric.

7. The method of claim 6, wherein applying the arbitration further comprises assigning weights to each of the sleep apnea metrics based on a purpose for the single sleep apnea metric.

8. The method of claim 1, comprising controlling an air supply device based on the single sleep apnea metric.

9. The method of claim 1, wherein applying the arbitration further comprises increasing the weighted value as more data becomes available.

10. The method of claim 1, comprising analyzing the physiological parameter data with a third pattern recognition feature to identify indications of sleep apnea and calculating a third sleep apnea metric with the third pattern recognition feature based on indications of sleep apnea identified by the third pattern recognition feature in the physiological parameter data.

11. The method of claim 10, comprising applying the arbitrator to the first, second, and third sleep apnea metrics to determine the single sleep apnea metric.

12. The method of claim 10, wherein analyzing the physiological parameter data with the first pattern recognition feature to identify indications of sleep apnea comprises analyzing a portion of the physiological parameter data.

13. A medical system, comprising:
    a microprocessor configured to process physiological parameter data; and
    a memory configured to store computer-readable instructions, wherein the contents of the memory comprises computer-readable instructions that if executed are configured to direct the microprocessor to:
        analyze the physiological parameter data to identify patterns indicative of sleep apnea using a first procedure for sleep apnea pattern recognition;
        quantify patterns identified using the first procedure with a first calculation of a first metric indicative of sleep apnea;
        analyze the physiological parameter data to identify patterns indicative of sleep apnea using a second procedure for sleep apnea pattern recognition, wherein the first procedure and the second procedure are different;
        quantify patterns identified using the second procedure with a second calculation of a second metric indicative of sleep apnea;
        apply arbitration to the first and second metrics to determine a single reporting metric, wherein applying the arbitration further comprises assigning a weighted value to each of the sleep apnea metrics based on a type of algorithm performed by the pattern recognition feature associated with each metric; and
        communicate the single reporting metric to an output feature.

14. The medical system of claim 13, comprising a sensor configured to produce the physiological parameter data.

15. The medical system of claim 13, wherein the physiological parameter data comprises a sequence indicative of blood oxygen level over a time period.

16. The medical system of claim 13, wherein the first procedure for sleep apnea pattern recognition is configured to analyze data comprising an encephalogram, an electromyogram, an extraoculogram, a chest wall plethysmogram, and/or an electrocardiogram.

17. The medical system of claim 13, wherein the first procedure for sleep apnea pattern recognition takes into account a portion of the physiological parameter data.

* * * * *